United States Patent
Doniwa et al.

(10) Patent No.: US 12,249,426 B2
(45) Date of Patent: Mar. 11, 2025

(54) HEALTHCARE SUPPORT SYSTEM AND RECORDING MEDIUM

(71) Applicant: KABUSHIKI KAISHA TOSHIBA, Tokyo (JP)

(72) Inventors: Kenichi Doniwa, Asaka (JP); Kosuke Haruki, Tachikawa (JP); Takahiro Tanaka, Akishima (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 312 days.

(21) Appl. No.: 17/016,740

(22) Filed: Sep. 10, 2020

(65) Prior Publication Data
US 2021/0125726 A1    Apr. 29, 2021

(30) Foreign Application Priority Data
Oct. 23, 2019    (JP) .................................. 2019-192850

(51) Int. Cl.
*G16H 50/30*    (2018.01)
*A61B 5/00*    (2006.01)

(52) U.S. Cl.
CPC ........... *G16H 50/30* (2018.01); *A61B 5/7275* (2013.01); *A61B 5/7435* (2013.01)

(58) Field of Classification Search
CPC ...... G16H 50/30; A61B 5/7275; A61B 5/7435
See application file for complete search history.

(56) References Cited

U.S. PATENT DOCUMENTS

| | | | |
|---|---|---|---|
| 8,409,104 B2 * | 4/2013 | Cobain | A61B 5/0205 600/481 |
| 2008/0183499 A1 * | 7/2008 | Tarkka | G16H 15/00 705/3 |

(Continued)

FOREIGN PATENT DOCUMENTS

| | | |
|---|---|---|
| EP | 1 192 896 A1 | 4/2002 |
| JP | 2006-163932 A | 6/2006 |

(Continued)

OTHER PUBLICATIONS

Snoek, J. et al., "Practical Bayesian Optimization of Machine Learning Algorithms," Advances in Neural Information Processing Systems 25 (NIPS 2012), 2012, http://papers.nips.cc/paper/4522-practical-bayesian-optimization-of-machine-learning-algorithms.pdf, 9 pages.

*Primary Examiner* — Mohamed Charioui
*Assistant Examiner* — Christine Y Liao
(74) *Attorney, Agent, or Firm* — Oblon, McClelland, Maier & Neustadt, L.L.P.

(57) ABSTRACT

According to one embodiment, a healthcare support system includes a memory and a hardware processor connected to the memory. The hardware processor predicts a risk value of a disease based on medical checkup data for a medical examinee. The hardware processor sets a reduction target for the risk value of the disease, and sets a plurality of second factors constituting search targets among a plurality of first factors relating to the disease and a search range for each of the second factors. The hardware processor searches, by using a predetermined search method, in the search range for each of the second factors, for a target value candidate of each of the second factors so that the risk value of the disease is brought close to the reduction target.

12 Claims, 8 Drawing Sheets

(56) References Cited

U.S. PATENT DOCUMENTS

| | | | |
|---|---|---|---|
| 2016/0283686 A1* | 9/2016 | Hu | ................. G06N 20/00 |
| 2017/0169329 A1 | 6/2017 | Doniwa et al. | |
| 2020/0111574 A1* | 4/2020 | Hosein | ................. G16H 10/60 |

FOREIGN PATENT DOCUMENTS

| | | |
|---|---|---|
| JP | 4499542 B2 | 7/2010 |
| JP | 2010-198411 A | 9/2010 |
| JP | 6470165 B2 | 2/2019 |
| WO | WO 2016/077727 A1 | 5/2016 |

* cited by examiner

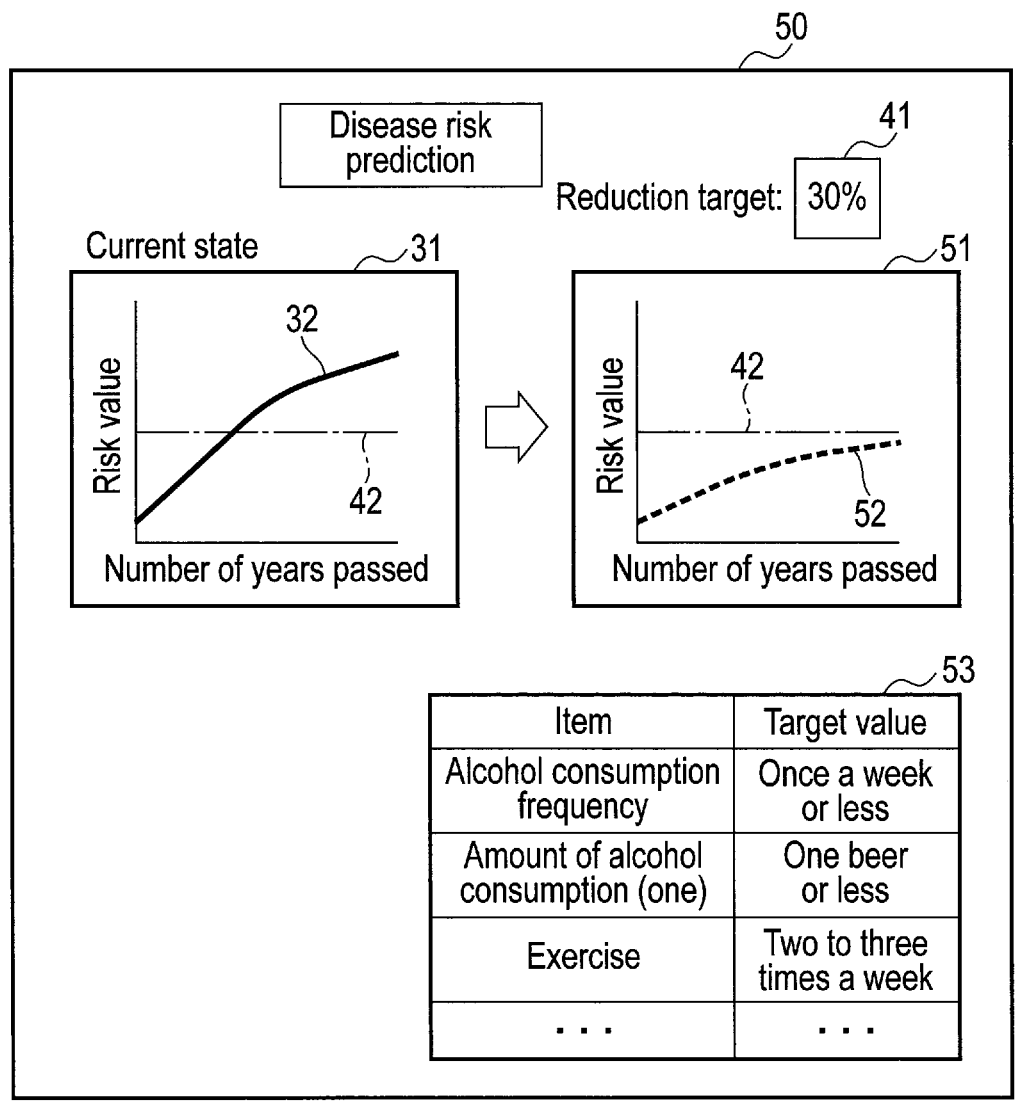
F I G. 5

Individual intention setting

| Item | Individual intention parameter |
|---|---|
| Exercise habit | 0.1 |
| Exercise intensity | 0.1 |
| Alcohol consumption frequency | 0.5 |
| Amount of alcohol consumption (one) | 0.5 |
| Smoking | 0.3 |
| Sleeping hours | 0.1 |
| ... | ... |

FIG. 6

| Item | Individual intention setting | Individual intention | | |
|---|---|---|---|---|
| Exercise habit | | ⊘ Occasional | ○ Regular | ○ Frequent |
| Exercise intensity | | ⊘ Low | ○ Medium | ○ High |
| Alcohol consumption frequency | | ○ Occasional | ⊘ Regular | ○ Frequent |
| Amount of alcohol consumption (one) | | ○ Small | ⊘ Medium | ○ Large |
| Smoking | | ○ Occasional | ⊘ Regular | ○ Frequent |
| Sleeping hours | | ⊘ Less than 5 hours ○ 5-6 hours ○ 6-7 hours ○ 7 or more hours | | |
| Diet type | | ⊘ Lots of meat ○ Lots of vegetables ○ Lots of dairy ○ Lots of salt | | |
| ... | | ... | | |

FIG. 7

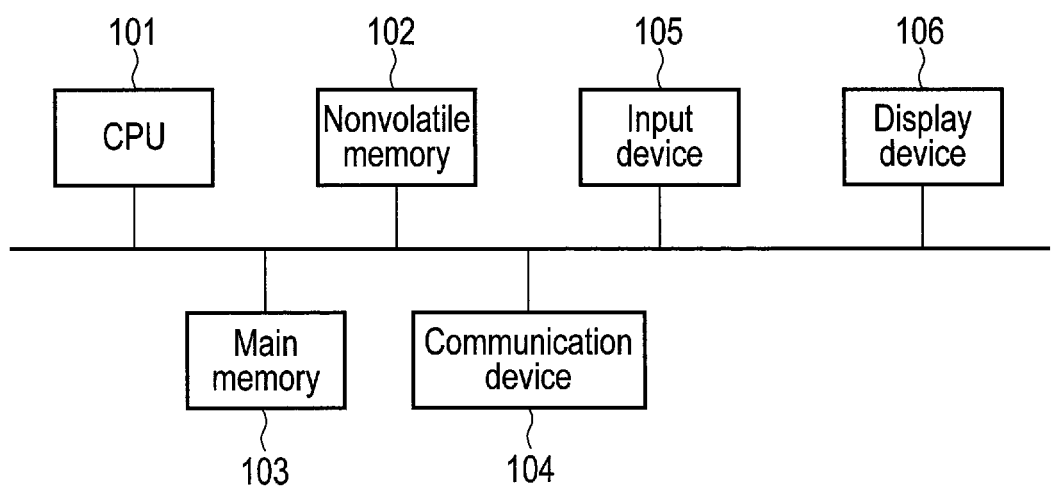
F I G. 10 ns of priority from Japanese Patent Application No. 2019-192850, filed Oct. 23, 2019, the entire contents of which are incorporated herein by reference.

HEALTHCARE SUPPORT SYSTEM AND RECORDING MEDIUM

CROSS-REFERENCE TO RELATED APPLICATIONS

This application is based upon and claims the benefit of priority from Japanese Patent Application No. 2019-192850, filed Oct. 23, 2019, the entire contents of which are incorporated herein by reference.

FIELD

Embodiments described herein relate generally to a healthcare support system and a recording medium.

BACKGROUND

In recent years, the business of predicting the risk of the onset of a specific disease from medical examination results, for example, has been developing. Here, in order to reduce a predicted disease risk, it is important for medical examinees to know what kind of targets to set in specific terms. Formulae for predicting the probability of a disease developing have been proposed. Using such prediction formulae makes it possible to recursively determine target values for each of the factors for reducing risk.

However, there are multiple disease-related factors and interactions between such factors. In the foregoing prediction formulae, the target values for each of the factors which are to reduce the disease risk must be examined comprehensively, which necessitates an enormous amount of calculation.

BRIEF DESCRIPTION OF THE DRAWINGS

FIG. 5 is a diagram illustrating an example of a UI screen which is displayed as a search result screen according to the embodiment.

FIG. 6 is a diagram illustrating an example of a UI screen which is displayed as an individual intention setting screen according to the embodiment.

FIG. 7 is a diagram illustrating another example of a UI screen which is displayed as an individual intention setting screen according to the embodiment.

FIG. 10 is a diagram illustrating an example of a hardware configuration of the healthcare support system according to the embodiment.

DETAILED DESCRIPTION

Figure 1:
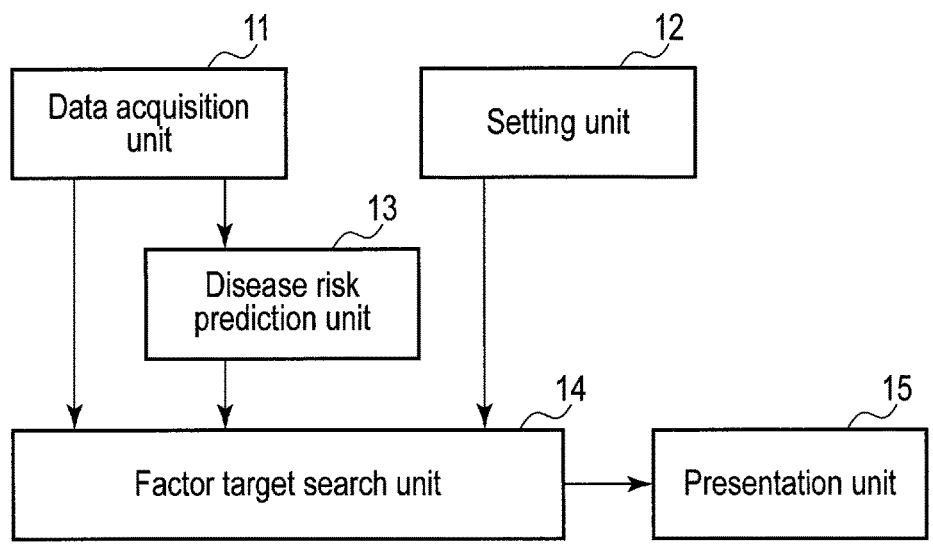
FIG. 1 is a block diagram illustrating a configuration of a healthcare support system according to an embodiment.

In general, according to one embodiment, a healthcare support system includes a memory and a hardware processor connected to the memory. The hardware processor predicts a risk value of a disease based on medical checkup data for a medical examinee. The hardware processor sets a reduction target for the risk value of the disease, and sets a plurality of second factors constituting search targets among a plurality of first factors relating to the disease and a search range for each of the second factors. The hardware processor searches, by using a predetermined search method, in the search range for each of the second factors, for a target value candidate of each of the second factors so that the risk value of the disease is brought close to the reduction target.

Hereinafter, embodiments will be explained with reference to the accompanying drawings.

Each figure is a schematic view of corresponding embodiment for its better understanding, and a shape, size, and ratio of the figure may be different from those of actual embodiment, and they may be arbitrarily changed based on the following description and may be shown schematically. The same elements may be referred to by the same referential numbers in the figures, and the detailed description thereof may be omitted.

The healthcare support system according to the present embodiment efficiently searches, using a Bayesian search method or another such search method, for target values of each of the factors for reducing disease risk by targeting people who are at a high risk of developing a specific disease in medical examinations, for example.

Here, "disease risk" is the probability of a specific disease developing. More precisely, "likelihood", which is output as a prediction result from a disease prediction engine (an algorithm), is defined as a risk value for the development of the disease. The higher the risk value, the higher the probability that the disease will develop.

Supposing that, according to a medical examination, the risk of a certain disease developing is 80%, for example. A reduction of this disease risk from 80% to 30% is considered. Factors affecting the reduction of the disease risk include factors which can be changed through individual effort and factors which cannot be changed through individual effort.

Factors Which Can be Changed Through Individual Effort body weight, HbA1c (hemoglobin A1c), fasting glucose level, exercise habit, etc.

Factors which cannot be changed through individual effort:

gender, age, height, etc.

Gender, age, height, and so forth, which are factors which cannot be changed through individual effort, do not enable a reduction in disease risk. Disease risk can be reduced by changing the factors which can be changed through individual effort.

It is considered that disease risk is reduced by changing five kinds of factors, namely, body weight, HbA1c, fasting glucose level, exercise habit, and alcohol consumption, for example. The values of such factors are assumed to lie within the following ranges:

Body weight: 21 values representing each kilogram in the range 50 kg to 70 kg,

HbA1c: 21 values in 0.1 increments in the range 5.0 to 7.0,

Fasting glucose level: 41 values in increments of 1 in the range 90 to 130,

Exercise habit: 4 values, namely, never, occasional habit, regular habit, and frequent habit, and Alcohol consumption: 4 values, namely, never, low-frequency, mid-frequency, and high-frequency.

When the effects of interactions between these five factors are also considered, disease risk must be predicted for combinations of the five factors.

The number of combinations is

21×21×41×4×4=289,296.

From among this enormous number of combinations, the target values of each of the factors must be determined in accordance with disease risk reduction targets such as, for example, a reduction in body weight to 60 kg, a reduction in HbA1c to 5.7, and a reduction in fasting glucose level to 100. Although the related factors are limited to five in this example, when the multiple factors are taken into account without such limitation, the amount of computation required in a factor search is then enormous. Hence, an efficient search for target values for each factor must be performed.

FIG. 1 is a block diagram illustrating a configuration of a healthcare support system according to an embodiment.

The healthcare support system according to the present embodiment includes a PC, a server computer, or the like, for example. This healthcare support system includes a function for setting a target value (reduction target) for reducing the risk of a specific disease developing, and a function for searching for a target value for each factor in order to achieve the reduction target. Although "diabetes" is described as a specific disease by way of example hereinbelow, various diseases designated as lifestyle diseases, such as, for example, "hypertension" and "dyslipidemia" constitute targets.

As illustrated in FIG. 1, this healthcare support system includes a data acquisition unit 11, a setting unit 12, a disease risk prediction unit 13, a factor target search unit 14, and a presentation unit 15.

The data acquisition unit 11 acquires, from a database (not illustrated), based on the ID or the like of a medical examinee who has undergone a medical examination, for example, medical examination data (hereinafter called medical checkup data) indicating a diagnosis result for the medical examinee. Note that, as the method for acquiring the medical checkup data, a method with which the medical checkup data of a medical examinee is fetched via a recording medium or a communication medium (not illustrated), for example, may be used.

The setting unit 12 sets target values (reduction targets) for reducing the risk of diabetes. Furthermore, the setting unit 12 sets various data required for search processing such as a plurality of factors serving as search targets among a plurality of diabetes-related factors, and a search range for such factors. Note that a plurality of factors that exist and pertain to each disease such as diabetes are defined as "first factors" and a plurality of factors which are selected as search targets among the first factors are defined as "second factors". In this system, target values relating to the second factors are searched for efficiently and presented.

The disease risk prediction unit 13 analyzes the medical checkup data obtained by the data acquisition unit 11 and predicts the risk of diabetes developing. Note that a method using a generally known disease prediction engine is employed as the method for predicting disease risk, a detailed description thereof is omitted here.

The factor target search unit 14 uses a predetermined search method to search for each of the factors constituting search targets and the target values, within a range, required to reduce the risk of diabetes developing. As the search method, the random method or the Bayesian method, or the like, for example, is used. The random method is a search method based on a uniform distribution that specializes in discrete parameter searches and initial value independent searches. The Bayesian method is a type of gradient method and is a search method based on a probability distribution that searches for an optimal solution close to a value obtained in a previous search and specializes in continuous parameter searches.

Details on the Bayesian method are disclosed in the paper "Practical Bayesian Optimization of Machine Learning Algorithms http://papers.nips.cc/paper/4522-practical-bayesian-optimization-of-machine-learning-algorithms.pdf".

The presentation unit 15 includes a display device, for example, and presents, in a viewable format, disease risk values which are obtained from medical checkup data. Furthermore, the presentation unit 15 presents target values for each of the factors which are obtained as search results by the factor target search unit 14. The presentation unit 15 presents the disease risk values obtained from medical checkup data and disease risk values constituting reduction targets so as to enable comparison therebetween.

Figure 2:
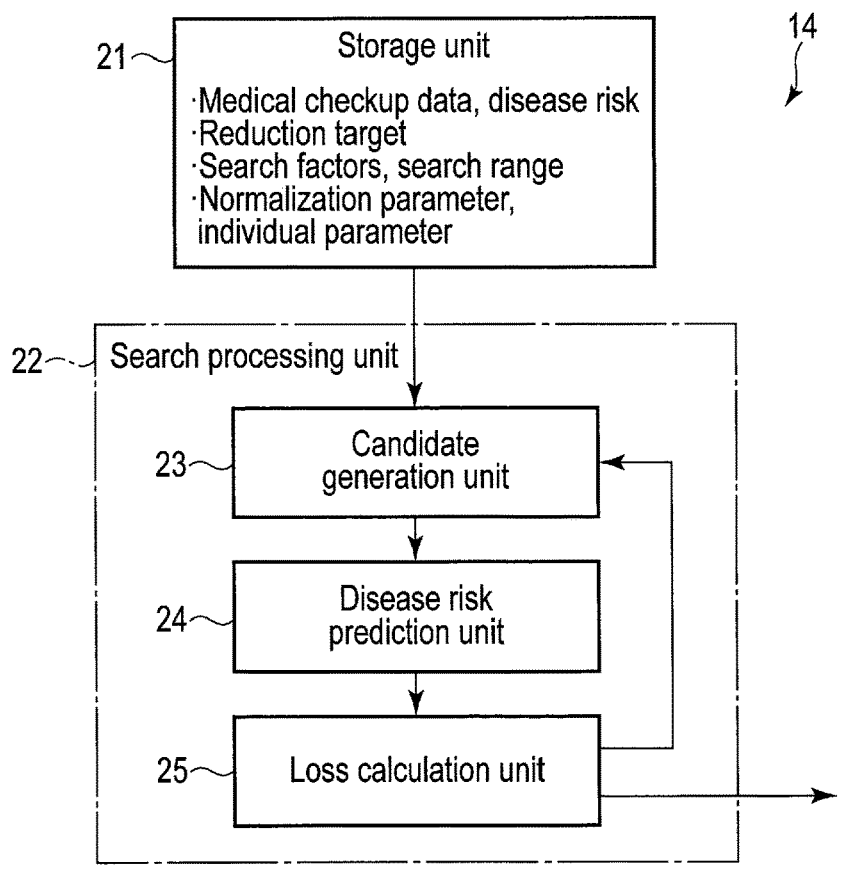
FIG. 2 is a block diagram illustrating details of a factor target search unit according to the embodiment.

FIG. 2 is a block diagram illustrating the details of the factor target search unit 14.

The factor target search unit 14 is configured from a storage unit 21 and a search processing unit 22. The storage unit 21 stores, in addition to the medical checkup data obtained by the data acquisition unit 11 and the disease risk obtained as a prediction result by the disease risk prediction unit 13, various data that is required for search processing such as reduction targets, search factors, a search range, normalization parameters, and individual parameters.

A reduction target is a target value indicating to what extent the disease risk is to be reduced. The search factors and search range are the respective types of the factors which have been selected as search targets and the ranges in which to search for the values of these factors. The normalization parameters and individual parameters are parameters which are used in a loss calculation, described subsequently. The normalization parameters are parameters for normalization of the value of each factor in the range 0.0 to 1.0. The individual parameters are parameters for reflecting individual intentions regarding each factor relating to lifestyle. The individual parameters are normalized in the range 0.0 to 1.0 like the normalization parameters.

The search processing unit 22 is the part that executes the search processing and has a candidate generation unit 23, a disease risk prediction unit 24, and a loss calculation unit 25.

The candidate generation unit 23 generates, based on the Bayesian search method or another such method, candidates for when a search is performed for target values of each of the factors in the search range. The disease risk prediction unit 24 predicts the risk of diabetes developing for the candidates generated by the candidate generation unit 23. The loss calculation unit 25 performs a loss calculation for each candidate generated by the candidate generation unit 23 and finds a target value for each of the factors from the calculation results. Note that this loss calculation will be described in detail subsequently.

The user interface (UI) screens used in this system will now be described. Note that each UI screen indicated hereinbelow may be displayed on the presentation unit 15 illustrated in FIG. 1 or may be displayed on an external terminal device via a network (not illustrated).

Figure 3:
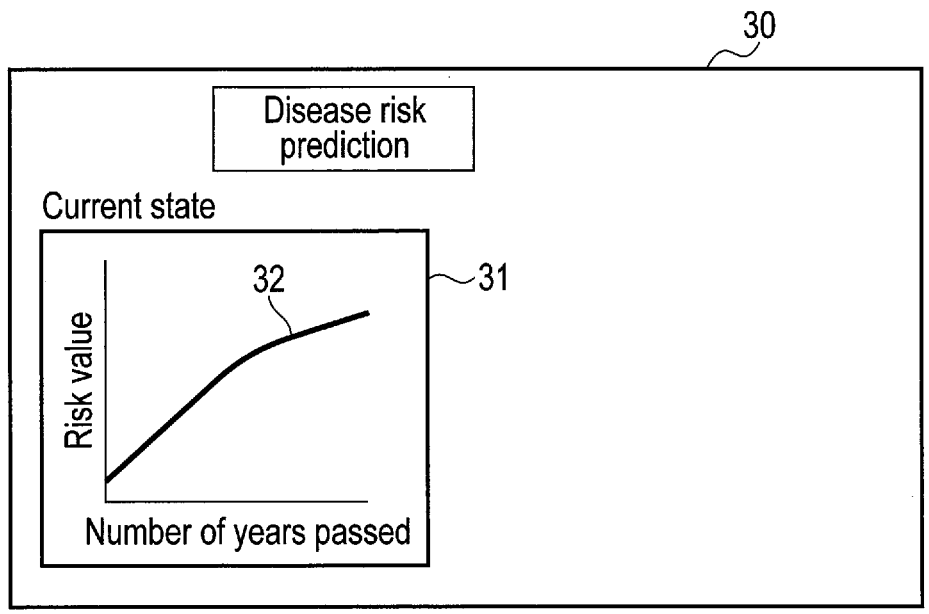
FIG. 3 is a diagram illustrating an example of a UI screen which is displayed as a disease risk prediction screen according to the embodiment.

FIG. 3 is a diagram illustrating an example of a UI screen 30 which is displayed as a disease risk prediction screen.

When the risk of a specific disease (diabetes here) developing is predicted by the disease risk prediction unit 13, the risk value obtained as the prediction result is displayed on the UI screen 30 in a graph format. The UI screen 30 is provided with a first graph display section 31 that indicates the relationship between the current risk value and the number of years passed, and displayed therein is a graph line 32 representing the current risk value. Note that, although the risk value is displayed in a graph format in this example, same may also be displayed in a table format, for example.

Figure 4:
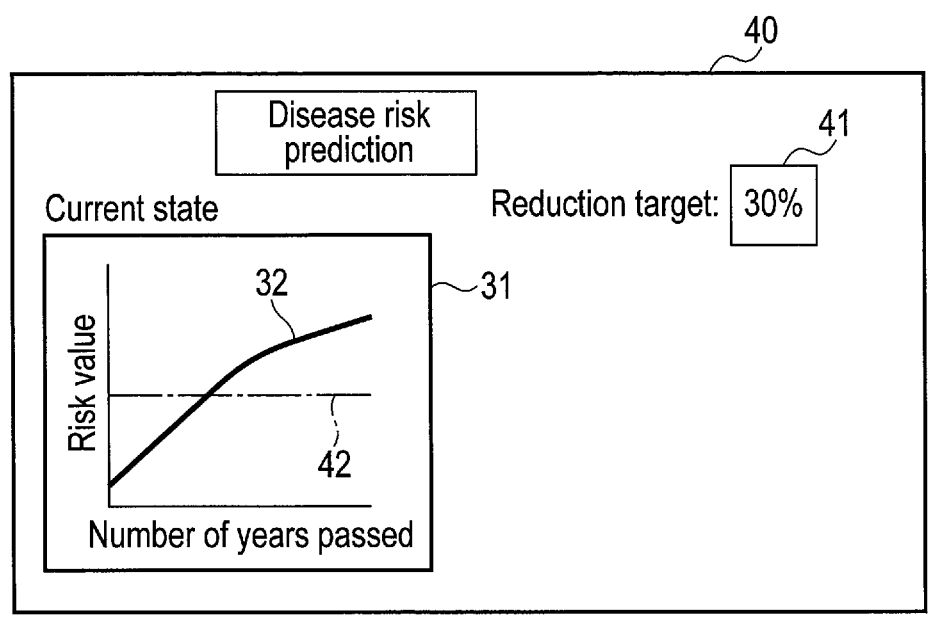
FIG. 4 is a diagram illustrating an example of a UI screen which is displayed as a reduction target setting screen according to the embodiment.

FIG. 4 is a diagram illustrating an example of a UI screen 40 which is displayed as a reduction target setting screen.

When reduction target settings are indicated using a predetermined operation, the UI screen 40 as illustrated in FIG. 4 is displayed. The UI screen 40 is provided with a numerical value input section 41 to which an optional value is input as a reduction target. In the example of FIG. 4, "30%" is input as the reduction target. This means that a reduction of the current risk value to 30% is being targeted.

Furthermore, a target line 42 corresponding to the reduction target is additionally displayed in the first graph display section 31 in accordance with the reduction target input. Note that the target line 42 may also be drawn directly in the first graph display section 31 by means of an operation such as a mouse operation, for example.

FIG. 5 is a diagram illustrating an example of a UI screen 50 which is displayed as a search result screen.

When a search for target values for each of the factors is performed by the factor target search unit 14, the search results are displayed on the UI screen 50 as illustrated in FIG. 5. The UI screen 50 is provided with a second graph display section 51 which indicates the relationship between a post-reduction risk value and the number of years passed and which displays a graph line 52 representing the post-reduction risk value so as to enable comparison with the graph line 32 representing the current risk value. It is thus possible to visually ascertain the extent of the effect produced when the reduction target is reached. Note that, although the current risk value and the post-reduction risk value are displayed in graph format here, same may also be displayed in table format.

Further, the UI screen 50 is provided with a target display section 53 in which each of the factor items and target values required for a risk reduction are displayed in table format. By incorporating the content displayed in the target display section 53 into lifestyle, a diabetes risk reduction of up to 30% can be expected. Note that, although each factor item and target value is displayed in table format in this example, same may also be displayed in graph format.

Note that, for a plurality of reduction targets, for example, the target values of each of the factors for achieving the reduction targets may be searched for in advance so that when a user (a medical examinee or the like) sets the reduction targets, the target values for each of the factors corresponding to the reduction targets can be displayed immediately. Thus, by performing a search for reduction targets in advance, the target values for each of the factors for realizing the reduction targets can be displayed in conjunction with risk values in accordance with the reduction target settings.

FIG. 6 is a diagram illustrating an example of a UI screen 60 which is displayed as an individual intention setting screen.

In this system, at the time of a search for target values of each of the factors for achieving the reduction targets that have been optionally set by a medical examinee, individual intentions regarding each lifestyle-related item can be reflected. Lifestyle-related items include, for example, "exercise habit", "exercise intensity", "alcohol consumption habit", "amount of alcohol consumption", "smoking", "sleeping hours", and so forth.

The UI screen 60 is provided with a parameter input section 61 for using parameters to input an individual intention for each item. The physician or medical examinee uses a keyboard operation or another such operation to input, using parameters, an individual intention regarding each item to the parameter input section 61. Parameter values have a range of 0.0 to 1.0. The lower the numerical value of an item, the stronger the individual intention indicated.

FIG. 7 is a diagram illustrating another example of a UI screen 70 which is displayed as an individual intention setting screen.

The UI screen 70 is provided with a selection section 71 for using a selection format to input an individual intention for each item. The physician or medical examinee uses an operation such as a mouse operation to input, in a selection format, an individual intention regarding each item in the selection section 71.

Next, the operation of the healthcare support system according to the present embodiment will be described.

Figure 8:
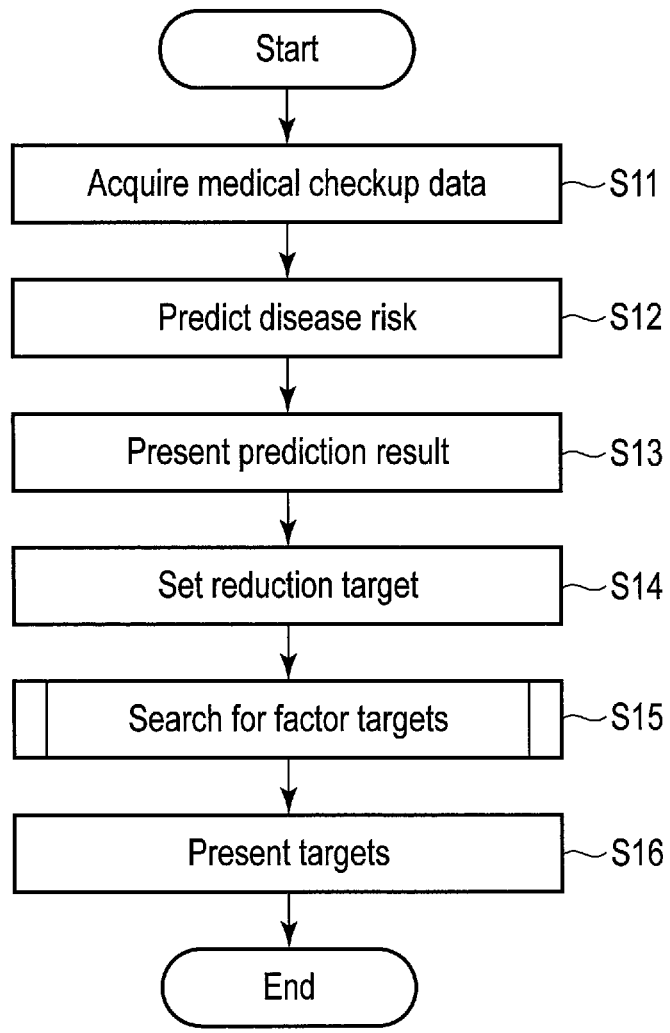
FIG. 8 is a flowchart illustrating the overall flow of the healthcare support system according to the embodiment.

FIG. 8 is a flowchart illustrating the overall flow of the healthcare support system. Note that the processing indicated in this flowchart is executed as a result of a CPU 101 (see FIG. 10), which is a computer, reading a program for implementing this system. The same is also true of the flowchart illustrated in FIG. 9.

As illustrated in FIG. 8, medical checkup data of a medical examinee is first acquired by the data acquisition unit 11 (step S11). More precisely, a database in which medical examination results are stored, for example, is used and the medical checkup data corresponding to the ID of the medical examinee is read from the database. This medical checkup data is provided to the disease risk prediction unit 13 and factor target search unit 14.

The disease risk prediction unit 13 predicts the risk of diabetes developing based on the medical checkup data (step S12). Note that a generally known disease prediction engine is used as the method for predicting the disease risk. The current risk value obtained by the disease risk prediction unit 13 as the prediction result is provided to the factor target search unit 14. Furthermore, as illustrated in FIG. 3, the graph line 32 representing the current risk value is displayed in the first graph display section 31 of the UI screen 30 (step S13).

Here, the physician or medical examinee sets target values (reduction targets) for reducing the risk of diabetes via the setting unit 12 (step S14). This state is represented by FIG. 4. In the example of FIG. 4, a reduction target "30%" is input to the numerical value input section 41 provided to the UI screen 40. When a reduction target is set, a search for target value candidates of each of the factors for achieving the reduction target is performed by the factor target search unit 14 (step S15). Note that the search processing by the factor target search unit 14 will be described in detail subsequently using FIG. 9.

When the target values for each of the factors are obtained by the factor target search unit 14, the target values are presented in a predetermined format via the presentation unit 15 (step S16). This state is represented by FIG. 5. In the example of FIG. 5, the graph line 52 representing a post-reduction risk value is displayed on the UI screen 50 so as to be compared with the graph line 32 representing the current risk value. Furthermore, each of the factor items and target values required for reducing the risk of diabetes are displayed in table format in the target display section 53.

Figure 9:
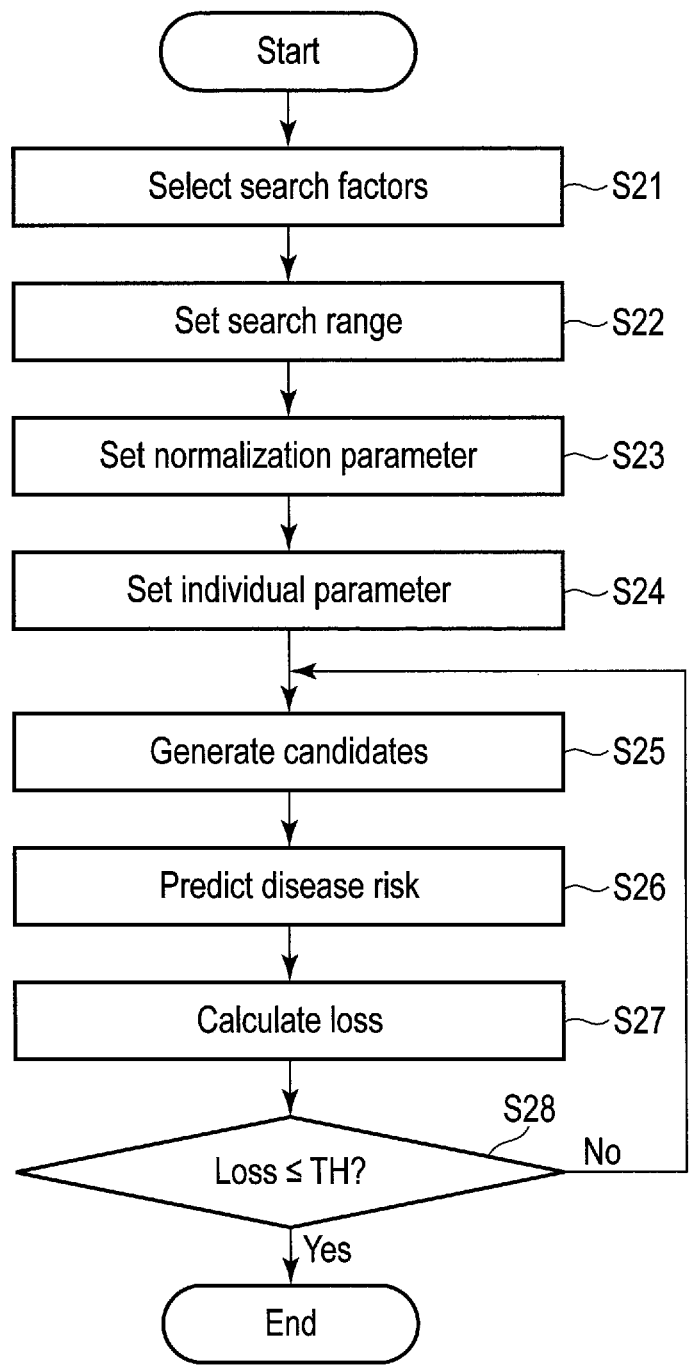
FIG. 9 is a flowchart illustrating a search processing operation which is executed in step S16 of FIG. 8.

FIG. 9 is a flowchart illustrating a search processing operation which is executed in step S16 of FIG. 8.

The medical checkup data obtained by the data acquisition unit 11 and the prediction result of the disease risk prediction unit 13 are provided to the factor target search unit 14 and stored in the storage unit 21. Further, the reduction targets set by the setting unit 12 are stored in the storage unit 21.

Here, when searching for target values for each of the factors, each of the factors serving as search targets among the factors relating to diabetes and a range for searching for target values for these factors are first set via the setting unit 12 (step S21). Information about the search factors and the search range set here is stored in the storage unit 21.

Diabetes is greatly affected by factors such as gender and age. However, these factors cannot be changed through individual effort. By excluding such unchangeable factors, only those factors which are changeable are optionally selected and serve as search targets. For example, four factors, namely, body weight, HbA1c, fasting glucose level, and exercise habit are selected as the search factors. This factor selection may be optionally performed by the physician, or the like, or selection may be performed based on information such as the feature amount importance of the disease prediction engine. If the physician or the like performs the factor selection, factors constituting search targets may be optionally selected via a UI screen for factor selection (not illustrated).

The search ranges may be predetermined by the factor types or may be optionally set by the physician or the like via a UI screen (not illustrated) for setting the search ranges.

A search range setting example is illustrated hereinbelow.

Search Range Setting Example

Body weight: 50 kg to 70 kg
HbA1c: 5.0 to 7.0
Fasting glucose level: 90 to 130
Exercise habit: never, occasional habit, regular habit, and frequent habit
Alcohol consumption: never, low-frequency, mid-frequency, and high-frequency Here, the ranges (scales) from which the values of each of the factors may be taken each have a different dimensionality. In other words, the range from which body weight values are taken is "50 to 70", and the range from which HbA1c values are taken is "5.0 to 7.0", for example. Hence, as preprocessing, the values of each factor must be normalized into data that enable comparison. Normalization methods include linear transformation, or the like, for example. In the present embodiment, normalization parameters for which 1 is a maximum value and 0 is a minimum value are set by the factor target search unit 14 and stored in the storage unit 21 (step S23).

Furthermore, individual parameters are set by the factor target search unit 14 and stored in the storage unit 21 (step S24). The individual parameters are parameters which are optionally set for each medical examinee. In other words, same are parameters for reflecting the intentions of the medical examinee regarding changing the content of particular items among items relating to lifestyle in order to reduce disease risk. For example, by configuring the individual parameter relating to the exercise habit item to be large for a disabled medical examinee, a search can be performed to minimize any change in the exercise habit as far as possible. Furthermore, by configuring the individual parameter corresponding to the alcohol consumption frequency item to be small for a medical examinee who is considered to be refraining from an alcohol consumption habit, a search can be performed for a change in alcohol consumption frequency.

Thus, individual intentions can be reflected, whether a medical examinee wants to reduce disease risk by changing their exercise habit or curb their disease risk by changing their alcohol consumption frequency. As the method for setting individual parameters, parameter values are input directly via the UI screen 60 as illustrated in FIG. 6.

Individual intentions among each of the items may also be input using a selection format via the UI screen 70 as illustrated in FIG. 7. For example, if the exercise habit from that point onward is changed to "frequent", the "frequent" exercise habit item in FIG. 7 is selected. If individual intentions among the items are thus configured using a selection format, the parameter values corresponding to the items selected are stored in the storage unit 21 as individual parameters.

When the various data required for search processing is stored in the storage unit 21, the following search processing is executed by the search processing unit 22.

The search processing unit 22 includes the candidate generation unit 23, the disease risk prediction unit 24, and the loss calculation unit 25. Using a predetermined search method, the candidate generation unit 23 generates, for each of the factors which have been selected as search targets, target value candidates within a search range for such factors (step S25). As the search method at such time, the random method or the Bayesian method, or the like, is used. Because the accuracy of the Bayesian method is higher than that of the random method, candidates are preferably generated using the Bayesian method. However, the Bayesian method uses previous search results, and hence a search is initially performed using the random method. Once initial candidates have been obtained using the random method, a search for the optimal candidates is performed using the Bayesian method.

Here, the disease risk prediction unit 24 predicts the risk of diabetes developing for the target value candidates of each factor which have been generated by the candidate generation unit 23 (step S26). The prediction processing performed here differs from that executed by the disease risk prediction unit 13. The disease risk prediction unit 13 predicts the risk of diabetes developing by using medical checkup data (examination values). In contrast, the disease risk prediction unit 24 predicts the risk of diabetes developing for each of the target value candidates of each factor. A loss calculation such as the following calculation is performed by the loss calculation unit 25 so that the risk values obtained as the prediction results of the disease risk prediction unit 24 are close to the reduction targets.

In other words, the loss calculation unit 25 executes the loss calculation indicated in formula (1) by using examination values for each factor which are obtained from medical checkup data, current risk values, reduction targets, target value candidates of each factor, risk values according to search candidates, normalization parameters and individual parameters.

$$\text{Loss}=\text{Loss1}+\alpha\times\text{Loss2} \tag{1}$$

Loss1 is a first loss which is calculated from the difference between the current risk value (a risk value which is predicted by the disease risk prediction unit 13 based on the medical checkup data for the medical examinee) and a risk value constituting the reduction target.

Loss2 is a second loss which is calculated from the difference between an examination value for each factor (a factor value which is obtained from medical checkup data for the medical examinee) and a target value candidate of each factor.

α is a parameter for adjusting the weighted ratios of Loss1 and Loss2. Loss is determined as a third loss which is obtained by adding together Loss1 and Loss2 using a weighting α.

Loss1 Calculation

In the case of a risk value for which the current risk value≤reduction target,
Loss1=0
In the case of a risk value for which the current risk value>reduction target, $$Loss1 = (\text{current risk value} - \text{risk value which is the reduction target})^2$$

Loss2 Calculation $$Loss2 = \Sigma(((Xi - Xi\_org) \times Xi\_std1 \times Xi\_std2)^2 / Num\_X)$$

$Xi$ is the target value candidate of the i-th factor of medical examinee $Xi\_org$ is the examination value of the i-th factor of medical examinee $Xi\_std1$ is the normalization parameter for normalizing loss for each factor $Xi\_std2$ is the individual parameter for reflecting individual intention $Num\_X$ is the number of factors constituting search targets The normalization parameter $Xi\_std1$ is intended to match the scale of each factor. For example, a height value is given as 160 cm, 170 cm, etc. An HbA1c value is given as 5.3, 5.6, 6.5, etc. The $Xi\_std1$ corresponding to each factor is suitably set and normalized in the range 0 to 1.

The individual parameter $Xi\_std2$ is a parameter for reflecting individual intentions in terms of which item each individual wants to focus on changing when lifestyle is changed in order to reduce disease risk. If $Xi\_std2$ is set low, a search is performed so as to change this item and if $Xi\_std2$ is set high, a search is performed so as to not change this item. If there is a desire to reduce disease risk by changing the exercise habit, the parameter corresponding to exercise habit may be set low. If there is a desire to reduce disease risk without changing alcohol consumption frequency, the parameter corresponding to alcohol consumption frequency may be set high.

If the third loss obtained by formula (1) is smaller than a preset threshold value TH (YES in step S28), the search processing unit 22 ends the search processing and outputs, as final values, the target values for each factor which have been obtained at this point in time. However, if the third loss is greater than the threshold value TH (NO in step S28), the search processing unit 22 repeats the search processing from step S25.

Note that the number of candidate searches is counted, and the search processing may be ended when the number of candidate searches reaches a preset number and the target values for each factor which have been obtained at this point in time may be output as final values.

The target values for each factor thus obtained are displayed so as to be viewable on the UI screen 50 as illustrated in FIG. 5 via the presentation unit 15. In the example of FIG. 5, the items and target values of each of the factors are displayed in table format, where "once a week or less" represents alcohol consumption frequency, "one beer or less" represents the amount of alcohol consumption, and "two or three times a week" represents exercise, and so forth. By incorporating this content into lifestyle, a reduction in the risk of diabetes developing of up to 30% can be expected.

Thus, according to the present embodiment, target value candidates of each factor are generated using a Bayesian search method or another such search method while performing the loss calculation indicated in formula (1) above, thereby obviating the need for an enormous amount of calculation and making it possible to efficiently determine and provide a medical examinee with the optimal target values. Formula (1) further includes a parameter for reflecting an individual intention. Hence, target values reflecting individual intentions such as an exercise habit or an alcohol consumption frequency, for example, can be provided.

Hardware Configuration

FIG. 10 is a diagram illustrating an example of a hardware configuration of a healthcare support system.

The healthcare support system according to the present embodiment is configured from a PC, a server computer, or the like, for example, and includes a CPU 101, a nonvolatile memory 102, a main memory 103, a communication device 104, an input device 105, a display device 106, and the like.

The CPU 101 is a hardware processor for controlling the operation of the various components that constitute a healthcare support system. The CPU 101 executes various programs which are loaded into the main memory 103 from the nonvolatile memory 102 that constitutes the storage device.

In addition to the operating system (OS), the programs executed by the CPU 101 include a program for executing the processing operations illustrated in the flowcharts of FIGS. 8 and 9 (hereinafter called the healthcare support program), or the like. Furthermore, the CPU 101 also executes a basic input-output system (BIOS), or the like, which is a program for hardware control, for example.

Note that some or all of the data acquisition unit 11, setting unit 12, disease risk prediction unit 13, factor target search unit 14, and presentation unit 15 illustrated in FIG. 1 are realized by causing the CPU 101 (the computer) to execute the healthcare support program.

The healthcare support program may be stored and distributed on a computer-readable recording medium or may be downloaded over a network. Note that some or all of the data acquisition unit 11, setting unit 12, disease risk prediction unit 13, factor target search unit 14, and presentation unit 15 may be realized by hardware such as an integrated circuit (IC) or may be realized as a configuration in which the software and hardware are combined.

The communication device 104 is a device that is configured to implement communication with an external device via a cable or wirelessly, for example. The input device 105 includes a keyboard and a mouse, or the like, for example, and is used when the user inputs various data and issues an instruction, and so forth. The display device 106 is a liquid crystal display, or the like, for example, and is a device for displaying various data and screens, and the like.

According to at least one of the foregoing embodiments, it is possible to provide a healthcare support system and program which enable target values for each of the factors required to reduce disease risk to be determined efficiently.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A healthcare support system comprising:
    a memory,
    a hardware processor connected to the memory, and
    a display device connected to the hardware processor,
    wherein the hardware processor is configured to:
        predict a risk value of a disease based on medical checkup data stored in the memory for a medical examinee;
        set a reduction target for the risk value of the disease;
        set a plurality of second factors constituting search targets among a plurality of first factors relating to the disease and a search range for each of the second factors;
        search, by using a random method or a Bayesian method, in the search range for each of the second factors, for a target value candidate of each of the second factors so that the risk value of the disease is brought close to the reduction target;
        execute search processing to reduce a loss value calculated based on the risk value of the disease and the reduction target, for each target value candidate of the second factors;
        calculate a third loss using a calculation formula for each target value candidate of the second factors;
        output, as a final value, a target value of each of the second factors with which the third loss is equal to or less than a preset threshold value; and
        generate a graphical user interface and display the graphical user interface on the display device, the graphical user interface displaying the target value for each of the second factors which is finally obtained by the search processing, displaying a current risk value predicted from the medical checkup data and a post-reduction risk value such that the current risk value is comparable with the post-reduction risk value, and displaying the reduction target, the graphical user interface displaying the current risk value and the post-reduction risk value side-by-side in a graph format or a table format and displaying the reduction target as a numerical value adjacent to the current risk value and the post-reduction risk value, and
    wherein the calculation formula adds together a first loss and a second loss using fixed weighting, the first loss being calculated from a difference between the current risk value and a risk value constituting the reduction target, and the second loss being calculated from the difference between an examination value for each of the second factors and the target value candidate of each of the second factors.

2. The healthcare support system according to claim 1, wherein the calculation formula comprises a normalization parameter configured to normalize the value of each of the second factors.

3. The healthcare support system according to claim 1, wherein the calculation formula comprises an individual parameter configured to reflect an individual intention regarding a plurality of items relating to lifestyle.

4. The healthcare support system according to claim 1, wherein the hardware processor is configured to end the search processing if the number of times of searches for the target value candidate of each of the second factors using the random method or the Bayesian method reaches a preset number.

5. The healthcare support system according to claim 1, wherein the hardware processor searches for the target value candidate of each of the second factors using the random method.

6. The healthcare support system according to claim 1, wherein the hardware processor searches for the target value candidate of each of the second factors using the Bayesian method.

7. The healthcare support system according to claim 1, wherein the graphical user interface displays the current risk value in the graph format.

8. The healthcare support system according to claim 1, wherein the graphical user interface displays the post-reduction risk value in the graph format.

9. The healthcare support system according to claim 1, wherein the graphical user interface displays the current risk value and the post-reduction risk value side-by-side in the table format.

10. The healthcare support system according to claim 1, wherein the graphical user interface displays a target display section in which each of factor items and target values required to achieve the risk reduction are displayed in a table format.

11. A non-transitory computer readable storage medium storing a computer program executed by a computer, the program being configured to control the computer to perform:
    predicting a risk value of a disease based on medical checkup data for a medical examinee;
    setting a reduction target for risk value of the disease;
    setting a plurality of second factors constituting search targets among a plurality of first factors relating to the disease and a search range for each of the second factors;
    searching, by using a random method or a Bayesian method, in the search range for each of the second factors, for a target value candidate of each of the second factors so that the risk value of the disease is brought close to the reduction target;
    executing search processing to reduce a loss value calculated based on the risk value of the disease and the reduction target, for each target value candidate of the second factors;
    calculating a third loss using a calculation formula for each target value candidate of the second factors;
    outputting, as a final value, a target value of each of the second factors with which the third loss is equal to or less than a preset threshold value; and
    generating a graphical user interface and displaying the graphical user interface on a display device, the graphical user interface displaying a target value for each of the second factors which is finally obtained by the search processing, displaying a current risk value predicted from the medical checkup data and a post-reduction risk value such that the current risk value is comparable with the post-reduction risk value, and displaying the reduction target, the graphical user interface displaying the current risk value and the post-reduction risk value side-by-side in a graph format or a table format and displaying the reduction target as a numerical value adjacent to the current risk value and the post-reduction risk value, wherein the calculation formula adds together a first loss and a second loss using fixed weighting, the first loss being calculated from a difference between the current risk value and a risk value constituting the reduction target, and the second loss being calculated from the difference between an examination value for each of the second factors and the target value candidate of each of the second factors.

12. A method executed by a computer, the method comprising:

predicting a risk value of a disease based on medical checkup data for a medical examinee;

setting a reduction target for the risk value of the disease;

setting a plurality of second factors constituting search targets among a plurality of first factors relating to the disease and a search range for each of the second factors;

searching, by using a random method or a Bayesian method, in the search range for each of the second factors, for a target value candidate of each of the second factors so that the risk value of the disease is brought close to the reduction target;

executing search processing to reduce a loss value calculated based on the risk value of the disease and the reduction target, for each target value candidate of the second factors;

calculating a third loss using a calculation formula for each target value candidate of the second factors;

outputting, as a final value, a target value of each of the second factors with which the third loss is equal to or less than a preset threshold value; and generating a graphical user interface and displaying the graphical user interface on a display device, the graphical user interface displaying a target value for each of the second factors which is finally obtained by the search processing, displaying a current risk value predicted from the medical checkup data and a post-reduction risk value such that the current risk value is comparable with the post-reduction risk value, and displaying the reduction target, the graphical user interface displaying the current risk value and the post-reduction risk value side-by-side in a graph format or a table format and displaying the reduction target as a numerical value adjacent to the current risk value and the post-reduction risk value, wherein the calculation formula adds together a first loss and a second loss using fixed weighting, the first loss being calculated from a difference between the current risk value and a risk value constituting the reduction target, and the second loss being calculated from the difference between an examination value for each of the second factors and the target value candidate of each of the second factors.

* * * * *